(12) United States Patent
Voegele et al.

(10) Patent No.: US 8,155,728 B2
(45) Date of Patent: Apr. 10, 2012

(54) MEDICAL SYSTEM, METHOD, AND STORAGE MEDIUM CONCERNING A NATURAL ORIFICE TRANSLUMINAL MEDICAL PROCEDURE

(75) Inventors: James W. Voegele, Cincinnati, OH (US); Robert M. Trusty, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1159 days.

(21) Appl. No.: 11/894,841

(22) Filed: Aug. 22, 2007

(65) Prior Publication Data

US 2009/0054761 A1 Feb. 26, 2009

(51) Int. Cl.
*A61B 5/05* (2006.01)
(52) U.S. Cl. ........ 600/424; 600/407
(58) Field of Classification Search ........ 600/407, 600/424, 425, 433; 606/34
See application file for complete search history.

(56) References Cited

U.S. PATENT DOCUMENTS

| | | | |
|---|---|---|---|
| 5,391,199 A | 2/1995 | Ben-Haim | |
| 5,398,691 A | 3/1995 | Martin et al. | |
| 5,497,934 A | 3/1996 | Brady et al. | |
| 5,575,288 A | 11/1996 | Sliwa, Jr. et al. | |
| 5,636,255 A | 6/1997 | Ellis | |
| 5,728,044 A | 3/1998 | Shan | |
| 5,729,129 A | 3/1998 | Acker | |
| 5,771,896 A | 6/1998 | Sliwa, Jr. et al. | |
| 5,772,594 A | 6/1998 | Barrick | |
| 5,836,869 A | 11/1998 | Kudo et al. | |
| 5,868,673 A | 2/1999 | Vesely | |
| 6,016,439 A | 1/2000 | Acker | |
| 6,092,526 A * | 7/2000 | LaFontaine et al. | 128/898 |
| 6,167,292 A | 12/2000 | Badano et al. | |
| 6,252,599 B1 | 6/2001 | Natsuko et al. | |
| 6,321,106 B1 | 11/2001 | Lemelson | |
| 6,381,485 B1 | 4/2002 | Hunter et al. | |
| 6,428,547 B1 | 8/2002 | Vilsmeier | |
| 6,456,735 B1 | 9/2002 | Sato et al. | |
| 6,491,702 B2 | 12/2002 | Heilbrun et al. | |
| 6,546,279 B1 | 4/2003 | Bova et al. | |

(Continued)

FOREIGN PATENT DOCUMENTS

DE 102005022901 11/2006

(Continued)

OTHER PUBLICATIONS

U.S. Appl. No. 11/524,216, filed Sep. 20, 2006, Voegele.

(Continued)

*Primary Examiner* — Michael Rozanski (57) ABSTRACT

A medical system includes a catheter, a sensor, 3-D image data representative of a patient, and a computer. The catheter has a catheter distal end insertable into a natural orifice of a body lumen of the patient. The sensor is disposable proximate the catheter distal end and is adapted to provide position data. The computer is adapted: to receive an indication from a user of a medical target selected for a medical procedure which uses at least the catheter and which is to be performed within the patient; and to indicate to the user position information of the catheter distal end relative to the medical target using at least the 3-D image data and the position data. A storage medium contains a program readable by a computer which instructs the computer to perform the previously described steps. A method for assisting a medical procedure performs the above-described steps.

8 Claims, 6 Drawing Sheets

U.S. PATENT DOCUMENTS

| | | | |
|---|---|---|---|
| 6,556,695 | B1 | 4/2003 | Packer et al. |
| 6,615,063 | B1 | 9/2003 | Ntziachristos et al. |
| 6,690,964 | B2 | 2/2004 | Bieger et al. |
| 6,773,402 | B2 | 8/2004 | Govari et al. |
| 7,366,562 | B2 | 4/2008 | Dukesherer et al. |
| 7,697,972 | B2 * | 4/2010 | Verard et al. ............... 600/424 |
| 7,764,985 | B2 | 7/2010 | McCombs et al. |
| 7,840,256 | B2 | 11/2010 | Lakin et al. |
| 2001/0029333 | A1 | 10/2001 | Shahidi |
| 2001/0044578 | A1 | 11/2001 | Ben-Haim et al. |
| 2002/0007108 | A1 | 1/2002 | Chen et al. |
| 2002/0087101 | A1 | 7/2002 | Barrick et al. |
| 2002/0156363 | A1 | 10/2002 | Hunter et al. |
| 2003/0065294 | A1 | 4/2003 | Pickup et al. |
| 2003/0139668 | A1 | 7/2003 | Ben-Haim et al. |
| 2003/0160721 | A1 | 8/2003 | Gilboa et al. |
| 2004/0101822 | A1 | 5/2004 | Wiesner et al. |
| 2004/0105979 | A1 | 6/2004 | Bayless |
| 2004/0167391 | A1 | 8/2004 | Solar et al. |
| 2005/0020878 | A1 | 1/2005 | Ohnishi et al. |
| 2005/0020918 | A1 | 1/2005 | Wilk et al. |
| 2005/0033164 | A1 | 2/2005 | Yatsuo et al. |
| 2005/0080333 | A1 | 4/2005 | Piron et al. |
| 2005/0085793 | A1 | 4/2005 | Glossop |
| 2005/0152836 | A1 | 7/2005 | Ashley et al. |
| 2005/0182295 | A1 | 8/2005 | Soper et al. |
| 2005/0196028 | A1 | 9/2005 | Kleen et al. |
| 2005/0203420 | A1 | 9/2005 | Kleen et al. |
| 2006/0052701 | A1 | 3/2006 | Carter et al. |
| 2006/0058644 | A1 | 3/2006 | Hoppe et al. |
| 2006/0064006 | A1 | 3/2006 | Strommer et al. |
| 2006/0089624 | A1 | 4/2006 | Voegele et al. |
| 2006/0089625 | A1 | 4/2006 | Voegele et al. |
| 2006/0089626 | A1 | 4/2006 | Voegele et al. |
| 2006/0142657 | A1 | 6/2006 | Quaid et al. |
| 2006/0149134 | A1 | 7/2006 | Soper et al. |
| 2006/0173299 | A1 | 8/2006 | Romley et al. |
| 2006/0183246 | A1 | 8/2006 | Wiesner et al. |
| 2006/0239544 | A1 | 10/2006 | Yankelevitz et al. |
| 2006/0245971 | A1 | 11/2006 | Burns et al. |
| 2006/0271056 | A1 | 11/2006 | Terrill-Grisoni et al. |
| 2007/0147705 | A1 | 6/2007 | Clune et al. |
| 2007/0173689 | A1 | 7/2007 | Ozaki et al. |
| 2007/0191707 | A1 | 8/2007 | Denittis |
| 2007/0270685 | A1 | 11/2007 | Kang et al. |
| 2008/0086051 | A1 | 4/2008 | Voegele |
| 2008/0118103 | A1 | 5/2008 | Pescatore et al. |
| 2008/0221434 | A1 | 9/2008 | Voegele |
| 2008/0232656 | A1 | 9/2008 | Voegele |
| 2008/0234544 | A1 | 9/2008 | Voegele |
| 2008/0234566 | A1 | 9/2008 | Voegele et al. |
| 2008/0234720 | A1 | 9/2008 | Chang et al. |
| 2008/0298655 | A1 | 12/2008 | Edwards |
| 2008/0319307 | A1 | 12/2008 | Voegele et al. |
| 2009/0161927 | A1 | 6/2009 | Mori et al. |

FOREIGN PATENT DOCUMENTS

| | | |
|---|---|---|
| EP | 0920838 | 6/1999 |
| EP | 1410758 | 4/2004 |
| EP | 1652470 | 5/2006 |
| FR | 2779339 | 12/1999 |

OTHER PUBLICATIONS

Invitrogen—Qdot In Vivo Imaging, 2006 Introgen Corporation, 5 pages, webpage.
Kodak—Kodak X-Sight Imaging Agent for In Vivo Applications, 2007, 3 pages, Webpage.
Hybrid Silica Technologies, Inc.—01. Hybrid Silica Technologies, Inc. (HST) Founded to Commercialize CU Dots Fluorescent Nanoparticles, 2004, by the Office of the Vice Provost for Research, Cornell University, 2 pages, Webpage.
Website document of Mimics Software from Materialise (8 pages) (date of first publication unknown).
EP, Supplementary European Search Report, European Application No. 08730689.0; 6 pages (Apr. 28, 2010).
PCT, International Preliminary Report on Patentability, International Application No. PCT/US2008/056043; 5 pages (Sep. 15, 2009).
PCT, International Preliminary Report on Patentability, International Application No. PCT/US2008/057323; 5 pages (Sep. 22, 2009).
PCT, International Preliminary Report on Patentability, International Application No. PCT/US2008/057322; 5 pages (Sep. 22, 2009).
PCT, International Preliminary Report on Patentability, International Application No. PCT/US2007/078832; 6 pages (Mar. 24, 2009).
PCT, International Preliminary Report on Patentability, International Application No. PCT/US2008/054933; 6 pages (Sep. 8, 2009).
US, Office Action, U.S. Appl. No. 11/716,465; 15 pages (Jun. 24, 2009).
US, Office Action, U.S. Appl. No. 11/716,465; 11 pages (Mar. 16, 2010).
US, Office Action, U.S. Appl. No. 11/726,653; 22 pages (May 28, 2010).
US, Office Action, U.S. Appl. No. 11/524,216; 21 pages (Aug. 19, 2008).
US, Office Action, U.S. Appl. No. 11/524,216; 20 pages (Jan. 22, 2009).
US, Advisory Action, U.S. Appl. No. 11/524,216; 3 pages (Apr. 15, 2009).
US, Office Action, U.S. Appl. No. 11/524,216; 19 pages (Jun. 23, 2009).
US, Office Action, U.S. Appl. No. 11/524,216; 16 pages (Mar. 3, 2010).
US, Advisory Action, U.S. Appl. No. 11/524,216; 3 pages (May 11, 2010).
US, Office Action, U.S. Appl. No. 11/726,257; 17 pages (Aug. 6, 2009).
US, Office Action, U.S. Appl. No. 11/726,257; 16 pages (Mar. 2, 2010).
Supplementary Partial European Search Report, European Patent Application No. 07842741 (8 pages) (Aug. 6, 2009).
International Search Report, International Application No. PCT/US2008/054933 (3 pages) (mailed Aug. 20, 2008; published Nov. 27, 2008).
International Search Report, International Application No. PCT/US2007/078832 (2 pages) (mailed Apr. 10, 2008; published Jul. 3, 2008).
Viergever, M.A. et al., "Integration of functional and anatomical brain images," *Biophy. Chem.*, vol. 68, pp. 207-219 (1997).
PCT, International Search Report, PCT/US08/57323 (Aug. 7, 2008).
PCT, International Search Report, PCT/US08/57322 (Aug. 18, 2008).
PCT, International Search Report, PCT/US08/56043 (Aug. 26, 2008).
Supplementary Partial European Search Report, European Application No. 07842741.6 (8 pages) (Aug. 6, 2009).
US, Office Action, U.S. Appl. No. 11/726,653 (Nov. 4, 2010).
US, Notice of Allowance, U.S. Appl. No. 11/726,653 (Aug. 17, 2011).
CN, Notification of First Office Action, Chinese Application No. 200780034771.0 (Aug. 11, 2010).
CN, Notification of First Office Action, Chinese Application No. 200880012795.0 (Oct. 20, 2010).
EP, Office Action, European Application No. 07842741.6 (Oct. 12, 2010).
EP, Search Report, European Application No. 08743996.4 (Apr. 8, 2011).
US, Office Action, U.S. Appl. No. 11/725,834 (Mar. 22, 2011).
US, Office Action, U.S. Appl. No. 11/726,653 (Feb. 18, 2011).
EP, Supplementary European Search Report, European Application No. 08743996.4 (Apr. 8, 2011).
EP, Decision to Grant, European Application No. 08730689.0 (Apr. 21, 2011).
PCT, International Preliminary Report on Patentability, International Application No. PCT/US2008/056043 (Sep. 15, 2009).
PCT, International Preliminary Report on Patentability, International Application No. PCT/US2008/054933 (Sep. 8, 2009).
PCT, International Preliminary Report on Patentability, International Application No. PCT/US2007/078832 (Mar. 24, 2009).

PCT, International Preliminary Report on Patentability, International Application No. PCT/US2008/057323 (Sep. 22, 2009).
PCT, International Preliminary Report on Patentability, International Application No. PCT/US2008/057322 (Sep. 22, 2009).
US, Office Action, U.S. Appl. No. 11/725,834 (Mar. 22, 2011).
US, Office Action, U.S. Appl. No. 11/726,653 (Feb. 18, 2011).
US, Office Action, U.S. Appl. No. 11/820,354 (Jun. 29, 2011).
US, Office Action, U.S. Appl. No. 11/725,834 (Aug. 1, 2011).

* cited by examiner

MEDICAL SYSTEM, METHOD, AND STORAGE MEDIUM CONCERNING A NATURAL ORIFICE TRANSLUMINAL MEDICAL PROCEDURE

FIELD OF THE INVENTION

The present invention is related generally to medical technology, and more particularly to a medical system, to a method, and to a storage medium containing a computer program, all concerning a natural orifice transluminal medical procedure.

BACKGROUND OF THE INVENTION

A physician typically accesses and visualizes tissue within a patient's gastrointestinal (GI) tract with a gastrointestinal endoscope (such as a gastroscope or a colonoscope) having a long, flexible insertion tube. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. The light-obtained images from a video camera at the distal end of the insertion tube are displayed on a monitor for use by the physician. Some endoscopes have one or two working channels in the insertion tube extending from a port in the handpiece to the distal end of the insertion tube. A physician may insert medical devices into the working channels to help diagnose or treat tissue within the patient. Non-scope type catheters are known which do not have a video camera and which either have a working channel for insertion of a medical device therein or have an attached end effector defining the distal end of the catheter. In one known procedure, a physician uses a tissue-piercing implement in an endoscope working channel to cut the lumen wall to medically treat patient tissue outside the lumen. The point to cut the lumen wall is based on the physician's knowledge of general human anatomy. In another known procedure, light from a vaginally-inserted endoscope is seen on the other side of the vaginal wall by a laparoscope inserted into the stomach to determine the point for the endoscope to be used to cut the vaginal wall.

Imagers are known for obtaining 3-D (three-dimensional) image data of a patient and for displaying images of the image data on a display monitor. Such images include, without limitation, ultrasound images, X-ray images, computerized tomography (CT) images, positive electron emission (PET) images, magnetic resonance (MRI) images, fluoroscope images, etc. Where needed, it is known to register these images with a real world object by placing a marker on the skin of the patient, wherein the marker has a predetermined shape, and wherein the marker is recognizable in the image data using pattern recognition software (e.g., a conventional segmentation subroutine).

Position sensors are known which are placed on medical instruments which are inserted into a patient allowing the position of the medical instrument to be tracked inside the patient. Such position sensors are part of known position sensing systems such as an AC-based system available from Biosense-Webster or a DC-based system available from Ascension Technology Corporation.

Still, scientists and engineers continue to seek improved medical systems, methods, and storage media containing computer programs, all concerning natural orifice transluminal medical procedures.

SUMMARY

A first expression of an embodiment of a medical system of the invention is for a medical system which includes a catheter, a sensor, 3-D image data which is of a patient and which is pre-acquired, and a computer. The catheter has a catheter distal end insertable into a natural orifice of a body lumen of the patient, wherein the catheter is adapted to provide light-obtained image data obtained from proximate the catheter distal end. The sensor is disposable proximate the catheter distal end and is adapted to provide position data. The computer is adapted: to receive an indication from a user of a medical target selected for a medical procedure which uses at least the catheter and which is to be performed within the patient; to display a first image of a first image representation of the light-obtained image data from a viewpoint of the catheter distal end; to receive an indication from the user when the catheter distal end is at each of a plurality of predetermined physiological landmarks spaced apart along and within the body lumen; and to indicate to the user position information of the catheter distal end relative to the medical target using at least the 3-D image data, the position data of the disposed sensor, and the indications from the user when the catheter distal end was at each of the plurality of predetermined physiological landmarks.

A first expression of a storage medium of the invention is for a storage medium which contains a program readable by a digital computer which instructs the digital computer: to receive an indication from a user of a medical target selected for a medical procedure which uses at least a catheter and which is to be performed within a patient, wherein the catheter has a catheter distal end inserted into a natural orifice of a body lumen of the patient, and wherein a sensor is disposed proximate the catheter distal end and is adapted to provide position data; to display a first image of a first image representation of light-obtained image data from a viewpoint of the catheter distal end wherein the light-obtained image data is obtained proximate the catheter distal end; to receive an indication from the user when the catheter distal end is at each of a plurality of predetermined physiological landmarks spaced apart along and within the body lumen; and to indicate to the user position information of the catheter distal end relative to the medical target using at least 3-D image data which is of the patient and which is pre-acquired, the position data, and the indications from the user when the catheter distal end was at each of the plurality of the predetermined physiological landmarks.

A first method of the invention is for a method for assisting a medical procedure, wherein the method includes: inserting a catheter distal end of a catheter into a natural orifice of a body lumen of a patient, wherein the catheter is adapted to provide light-obtained image data obtained from proximate the catheter distal end; providing position data of a sensor disposed proximate the catheter distal end; obtaining 3-D image data which is of the patient and which is pre-acquired; receiving an indication from a user of a medical target selected for the medical procedure, wherein the medical procedure uses at least the catheter and is to be performed within the patient; displaying a first image of a first image representation of the light-obtained image data from a viewpoint of the catheter distal end; receiving an indication from the user when the catheter distal end is at each of a plurality of predetermined physiological landmarks spaced apart along and within the body lumen; and indicating to the user position information of the catheter distal end relative to the medical target using at least the 3-D image data, the position data, and the indications from the user when the catheter distal end was at each of the plurality of predetermined physiological landmarks.

A broader second expression of an embodiment of a medical system of the invention is for a medical system including a catheter, a sensor, 3-D image data which is representative of a patient, and a computer. The catheter has a catheter distal end insertable into a natural orifice of a body lumen of the patient. The sensor is disposable proximate the catheter distal end and is adapted to provide position data. The computer is adapted: to receive an indication from a user of a medical target selected for a medical procedure which uses at least the catheter and which is to be performed within the patient; and to indicate to the user position information of the catheter distal end relative to the medical target using at least the 3-D image data and the position data of the disposed sensor.

A broader second expression of a storage medium of the invention is for a storage medium which contains a program readable by a digital computer which instructs the digital computer: to receive an indication from a user of a medical target selected for a medical procedure which uses at least a catheter and which is to be performed within the patient, wherein the catheter has a catheter distal end inserted into a natural orifice of a body lumen of a patient, and wherein a sensor is disposed proximate the catheter distal end and is adapted to provide position data; and to indicate to the user position information of the catheter distal end relative to the medical target using at least 3-D image data which is representative of the patient and the position data.

A broader second method of the invention is for a method for assisting a medical procedure, wherein the method includes: inserting a catheter distal end of a catheter into a natural orifice of a body lumen of a patient; providing position data of a sensor disposed proximate the catheter distal end; obtaining 3-D image data which is representative of the patient; receiving an indication from a user of a medical target selected for the medical procedure, wherein the medical procedure uses at least the catheter and is to be performed within the patient; and indicating to the user position information of the catheter distal end relative to the medical target using at least the 3-D image data and the position data.

Several benefits and advantages are obtained from one or more of the expressions of the embodiment of the system, the expressions of the storage medium, and the methods of the invention. In one example, the catheter is a gastroscope insertion tube whose distal end is disposed in the stomach of a patient, the medical target is a tumor on an organ outside of, but close to, the stomach. In this example, the position information of the insertion-tube distal end relative to the medical target assists the user in aligning the distal end in the stomach a short distance from the tumor. When the indicated alignment and distance are acceptable, the user, in this example, then extends a tissue-piercing implement from a working channel of the gastroscope beyond the insertion-tube distal end to cut through the stomach wall to reach and medically treat the nearby tumor with the point to cut the stomach being more accurately determined than relying on the user's knowledge of general human anatomy and being determined without requiring a second scope on the other side of the stomach wall. This also avoids having to make an external incision on the patient as is required in open-surgery and laparoscopic procedures.

DETAILED DESCRIPTION

Before explaining the expressions of an embodiment of a medical system, the expressions of a storage medium, and the methods of the present invention in detail, it should be noted that each is not limited in its application or use to the details of construction and arrangement of parts, instructions, and steps illustrated in the accompanying drawings and description. The illustrative system embodiment, storage medium, and methods of the invention may be implemented or incorporated in other embodiments, storage media, methods, variations, and modifications, and may be practiced or carried out in various ways. Furthermore, unless otherwise indicated, the terms and expressions employed herein have been chosen for the purpose of describing the illustrative expressions and methods of the present invention for the convenience of the reader and are not for the purpose of limiting the invention.

It is further understood that any one or more of the following-described expressions of a medical system embodiment, expressions of a storage medium, methods, implementations, etc. can be combined with any one or more of the other following-described expressions of a medical system embodiment, expressions of a storage medium, methods, implementations, etc.

An embodiment of a medical system 10 of the invention is shown in FIGS. 1-4. A first expression of the system embodiment of FIGS. 1-4 is for a medical system 10 including a catheter 12, a sensor 14, 3-D image data 16 which is of a patient 18 and which is pre-acquired, and a computer 20. The catheter 12 has a catheter distal end 22 insertable into a natural orifice 24 of a body lumen 26 of the patient 18, wherein the catheter 12 is adapted to provide light-obtained image data 28 obtained from proximate the catheter distal end 22. The sensor 14 is disposable proximate the catheter distal end 22 and is adapted to provide position data. The computer 20 is adapted: to receive an indication from a user of a medical target 30 selected for a medical procedure which uses at least the catheter 12 and which is to be performed within the patient 18; to display a first image 32 of a first image representation of the light-obtained image data 28 from a viewpoint of the catheter distal end 22; to receive an indication from the user when the catheter distal end 22 is at each of a plurality of predetermined physiological landmarks 34, 36, 38 and 40 spaced apart along and within the body lumen 26; and to indicate to the user position information 44 of the catheter distal end 22 relative to the medical target 30 using at least the 3-D image data 16, the position data of the disposed sensor 14, and the indications from the user when the catheter distal end 22 was at each of the plurality of predetermined physiological landmarks 34-40. It is noted that the sensor 14 may be a wired or wireless sensor. It is also noted that "light-obtained image data" is electromagnetic-radiation-obtained image data such as visible light-obtained image data, infrared light-obtained image data, and ultraviolet light-obtained image data.

In one enablement of the first expression of the medical system embodiment of FIGS. 1-4, the computer 20 is adapted: to calculate a position of the sensor 14 indexed to the patient 18 by calculating a position of the sensor 14 indexed to a reference coordinate system and by indexing the reference coordinate system to the patient 18 using at least the position data and the indications from the user when the catheter distal end 22 was at each of the plurality of predetermined physiological landmarks 34-40; to create the first image representation of the patient 18 indexed to the patient 18 and from a viewpoint of the catheter distal end 22 using at least the light-obtained image data 28 and the calculated position of the sensor 14 indexed to the patient 18; and to display on one of at least-one display monitor 46 and 48 the first image 32 of the first image representation.

In one variation, the computer 20 is adapted: to identify the physiological landmarks 34-40 within the 3-D image data 16; to create a second image representation of the patient 18 indexed to the patient 18 from a viewpoint of the catheter distal end 22 using at least the 3-D image data 16, the identified physiological landmarks 34-40, the indications from the user when the catheter distal end 22 was at each of the predetermined physiological landmarks 34-40, and the calculated position of the sensor 14 indexed to the patient 18; and to display on one of the at least-one display monitor 46 and 48 a second image 50 of the second image representation. In the variation, the first image 32 may be called a scope view, wherein the second image 50 may be said to correspond to the scope view, and wherein the second image 50 (and the first image 32) may be manipulated by the user manipulating the catheter distal end 22.

In one modification, the at-least-one display monitor 46 and 48 includes first and second display monitors 46 and 48, wherein the first image 32 is displayed on the first display monitor 46, and wherein the second image 50 is displayed on the second display monitor 48. In one example, the computer 20 is adapted to morph the second image representation using the first image representation as a reference image representation. In one illustration, the second image 50 is a semi-transparent image. In a different modification, not shown, a registered overlay image of the first and second image representations is displayed on a single display monitor, wherein the first image is given a tissue translucency upon which is overlaid the second image.

It is noted that in the first expression of the medical system embodiment of FIGS. 1-4, the second image 50 is from pre-acquired image data, that the first image 32 is from real-time image data, and that the position data is real-time position data.

In one implementation, the position information 44 includes alignment information of the catheter distal end 22 relative to the medical target 30 and includes distance information of the catheter distal end 22 relative to the medical target 30 when the catheter distal end 22 is aligned with the medical target 30. Other types of position information 44 (such as, and without limitation, alignment-only position information or distance-only position information) are left to the artisan. In one example, the computer 20 is adapted: to show the medical target 30 as a colored dot in the second image 50; to show the line-of-sight (such as that of a video camera) of the catheter distal end 22 as cross-hairs 54 in the information window 52, to show an alignment dot 30' in the information window 52 wherein the catheter distal end 22 is aligned with the medical target 30 when the cross-hairs 54 are aligned on the alignment dot 30', and to show a number 56 indicating the distance information in the information window 52.

In the same or a different implementation, the computer 20 is adapted to display in the second image 50 only user-selected ones of body systems (such as the GI tract, the vascular system, etc.) and organs thereof (such as the stomach, liver, etc.) from the 3-D image data 16 by using touch-screen buttons (not shown) appearing in the information window 52. In one variation, separate top, front, and side 2-D plane views (not shown) and/or a 3-D (orthogonal) view may be displayed from the 3-D image data 16 by using touch-screen buttons (not shown) appearing in the information window 52. In one modification, each view would include a colored dot representing the medical target 30. In one example, the computer 20 also has image manipulation tools (for image sizing, image cropping, image cutting and pasting, etc.) such as those available from Cedara Software Corporation of Mississauga, Ontario, Canada.

In one application of the first expression of the medical system embodiment of FIGS. 1-4, the catheter 12 is a flexible endoscope insertion tube 58, wherein the wherein the insertion tube 58 has a first working channel 60, wherein the sensor 14 is insertable into the first working channel 60 and is translatable to proximate the catheter distal end 22, and wherein the insertion tube 58 has a second working channel 62 adapted to receive a tissue-piercing implement 64. In a different application, not shown, the sensor and/or the tissue-piercing implement is attached to the catheter proximate the catheter distal end. In another different application, not shown, the catheter is equipped with at least one exterior rail extending to proximate the catheter distal end, and the sensor and/or the tissue-piercing implement (such as a tissue-piercing implement equipped with a retractable protective cover) is adapted to be coupled to a corresponding rail and to be translated along the corresponding rail to proximate the catheter distal end. In one variation and without limitation, medical treatment (such as radiofrequency treatment and/or cryogenic treatment), medical drug delivery, and/or other medical implements (such as a grasper) are translatable to, or are attached to, the catheter distal end.

In one employment of the first expression of the medical-system embodiment of FIGS. 1-4, the medical target 30 is located outside the body lumen 26. In another employment, not shown, the medical target is located inside the body lumen such as a downstream blockage of the body lumen not yet seen in a scope-view first image from an upstream-located insertion tube or such as a polyp located beyond the maximum insertion length of the insertion tube unless the tissue-piercing implement is used to allow the insertion tube to leave and re-enter the GI tract bypassing some lengthy GI-tract convolutions.

An example of light-obtained image data 28 includes, without limitation, video image data from a video camera. Examples of 3-D image data 16 include ultrasound image data, X-ray image data, computerized tomography (CT) image data, positive electron emission (PET) image data, magnetic resonance (MRI) image data, and fluoroscope image data. An example of a computer program which creates a manipulative 3D display image from 2D CT-scans and MRI-scans is Mimics available from Materialise of Ann Arbor, Mich. Examples of a display monitor 46 and 48 include, without limitation, a computer monitor, a goggle display screen, and a room wall upon which projected images are displayed.

Examples of catheters 12 which are insertable into a natural orifice 24 of a body lumen 26 include, without limitation, the insertion tubes of: gastrointestinal endoscopes such as gastroscopes and colonoscopes; bronchoscopes; laryngoscopes; cystoscopes; and nephroscopes. Examples of appropriate body lumens 26 of a patient 18 include, without limitation, the upper GI (gastrointestinal) tract, the lower GI tract, the reproductive tract, the auditory tract, a lung, and a urinary tract. In one variation, not shown, the catheter is equipped with a centering means, such as a balloon, so the catheter will travel down the center of the body lumen.

Examples of sensors 14 adapted to provide position data include, without limitation, the position sensors of the AC-based position sensing system available from Biosense-Webster and the DC-based position sensing system available from Ascension Technology Corporation. The Biosense-Webster and Ascension-Technology sensors are adapted to provide position data through their respective position sensing systems. It is noted that, as used in describing the system embodiment of FIGS. 1-2, the term "position" includes up to six degrees of freedom so that calculating position includes calculating a two-dimensional or three-dimensional translation and two or three degrees of orientation of the sensor 16 with respect to a reference coordinate system or with respect to the patient 18. A description of the operation of an embodiment of a sensor 14 adapted to provide position data with respect to a reference coordinate system is found in US Patent Application Publication 2006/0089624.

Examples of predetermined physiological landmarks 34-40 include, without limitation, the aditus of the larynx, the base of the epiglottis, the most proximal portion of the thyroid cartilage, and the esophageal and gastric junction.

In one illustration of the first expression of the medical system embodiment of FIGS. 1-4, the sensor 14 is considered to be a position sensor of a Biosense Webster positioning sensing system and a transmitter, not shown, of such system is used by the computer 20 for a reference coordinate system for position data from the sensor 14. Thus, the computer 20 can index (i.e., register) the position data of the sensor 16 to the reference coordinate system. The light-obtained image data 28 is obtained from a viewpoint of the catheter distal end 22, such as the position of a video camera's light-entry lens 66 disposed on the catheter distal end 22, which can be related to the position of the sensor 14 disposed proximate the catheter distal end 22 and hence related to the reference coordinate system. Thus, the computer 20 can index the light-obtained image data 28 to the reference coordinate system. By using the indications from the user when the catheter distal end 22 was at each of the predetermined physiological landmarks 34-40, the computer 20 can index the reference coordinate system to the patient 18. Thus the computer 20 can index the light-obtained image data 28 to the patient 18 from a viewpoint of the catheter distal end 22.

In this illustration, the predetermined physiological landmarks 34-40 in the 3-D image data 16 are identified by a conventional segmentation subroutine running on the computer 20. By using the indications from the user when the catheter distal end 22 was at each of the predetermined physiological landmarks 34-40 and the calculated position of the sensor indexed to the patient 18, the computer 20 can index the 3-D image data 16 to the patient 18. By also using the known position of the sensor 14 relative to the position of the video camera's light-entry lens 66, the computer 20 can index the 3-D image data 16 to the patient 18 from the viewpoint of the catheter distal end 22.

A broader second expression of the medical system embodiment of FIGS. 1-4 is for a medical system 10 including a catheter 12, a sensor 14, 3-D image data 16 which is representative of a patient 18, and a computer 20. The catheter 12 has a catheter distal end 22 insertable into a natural orifice 24 of a body lumen 26 of the patient 18. The sensor 14 is disposable proximate the catheter distal end 22 and is adapted to provide position data. The computer 20 is adapted: to receive an indication from a user of a medical target 30 selected for a medical procedure which uses at least the catheter 12 and which is to be performed within the patient 18; and to indicate to the user position information 44 of the catheter distal end 22 relative to the medical target 30 using at least the 3-D image data 16 and the position data of the disposed sensor 14.

It is noted, that in the broader second expression of the medical system embodiment, the 3-D image data 16 may be of a generic patient, such as a generic patient having a similar sex, height, weight, body build, etc. as the actual patient 18, and that such generic-patient 3-D image data may, in one example, be morphed to conform to the actual patient 18 based upon indications from the user when the catheter distal end 22 was at each of a plurality of the predetermined physiological landmarks 34-40. Although not shown, it is noted that a second sensor (similar to sensor 14) and a man-made fiducial marker (having a shape identifiable in 3-D image data by the computer 20 using conventional segmentation software) may be used to index the 3-D data 16 to the reference coordinate system eliminating the need for identifying physiological landmarks, as can be appreciated by those skilled in the art, wherein the position of the fiducial marker is known with respect to the second sensor and wherein the fiducial marker appears in the 3-D image data 16. When using the fiducial marker and the second sensor, the light-obtained image data 28 and the 3-D image data 16 would be indexed to the reference coordinate system from the viewpoint of the catheter distal end 22.

In one employment of the second broader expression of the medical system embodiment of FIGS. 1-4, the catheter 12 is adapted to support a tissue-piercing implement 64, and the medical procedure includes piercing the body lumen 26 using the catheter-supported tissue-piercing implement 64. In one variation, the 3-D image data 16 is 3-D image data of the patient 18. In one modification, the medical system 10 also includes at least one display monitor 46 and 48, wherein the catheter 12 is adapted to provide light-obtained image data 28 obtained from proximate the catheter distal end 22, and wherein the computer 20 is adapted: to create a first image representation from a viewpoint of the catheter distal end 22 using at least the light-obtained image data 28; and to display on one of the at-least-one display monitor 46 and 48 a first image 32 of the first image representation.

In the same or a different employment, the 3-D image data 16 is pre-acquired. In one variation, the computer 20 is adapted: to create a second image representation from the viewpoint of the catheter distal end 22 using at least the 3-D image data 16; and to display on one of the at-least-one display monitor 46 and 48 a second image 50 of the second image representation. In one modification, the catheter distal end 22 is adapted to be articulated by the user from outside the body lumen 26.

Previously-described implementations, examples, etc. are equally applicable to the second broader expression of the medical system embodiment. In one utilization of the second broader expression of the medical system embodiment, there is no light-obtained image data 28 (which allows for a smaller size catheter), and there is no display of 3-D image data 16.

A first expression of a storage medium 68 of the invention is for a storage medium 68 which contains a program readable by a digital computer 20 which instructs the digital computer 20: to receive an indication from a user of a medical target 30 selected for a medical procedure which uses at least a catheter 12 and which is to be performed within a patient 18, wherein the catheter 12 has a catheter distal end 22 inserted into a natural orifice 24 of a body lumen 26 of the patient 18, and wherein a sensor 14 is disposed proximate the catheter distal end 22 and is adapted to provide position data; to display a first image 32 of a first image representation of light-obtained image data 28 from a viewpoint of the catheter distal end 22, wherein the light-obtained image data 28 is obtained proximate the catheter distal end 22; to receive an indication from the user when the catheter distal end 22 is at each of a plurality of predetermined physiological landmarks 34, 36, 38, and 40 spaced apart along and within the body lumen 26; and to indicate to the user position information 44 of the catheter distal end 22 relative to the medical target 30 using at least 3-D image data 16 which is of the patient and which is pre-acquired, the position data, and the indications from the user when the catheter distal end 22 was at each of the plurality of the predetermined physiological landmarks 34-40.

In one enablement of the storage medium embodiment, the program instructs the digital computer 20: to calculate a position of the sensor 14 indexed to the patient 18 by calculating a position of the sensor 14 indexed to a reference coordinate system and by indexing the reference coordinate system to the patient 18 using at least the position data and the indications from the user when the catheter distal end 22 was at each of the plurality of predetermined physiological landmarks 34-40; to create the first image representation of the patient 18 indexed to the patient 18 and from a viewpoint of the catheter distal end 22 using at least the light-obtained image data 28 and the calculated position of the sensor 14 indexed to the patient 18; and to display on one of at least-one display monitor 46 and 48 the first image 32 of the first image representation.

In one variation, the program instructs the digital computer 20: to identify the physiological landmarks 34-40 within the 3-D image data 16; to create a second image representation of the patient 18 indexed to the patient 18 from a viewpoint of the catheter distal end 22 using at least the 3-D image data 16, the identified physiological landmarks 34-40, the indications from the user when the catheter distal end 22 was at each of the plurality of predetermined physiological landmarks 34-40; and the calculated position of the sensor 14 indexed to the patient 18; and to display on one of the at least-one display monitor 46 and 48 a second image 50 of the second image representation.

Previously-described implementations, examples, etc. are equally applicable to the first expression of the storage medium 68. Examples of storage media 68 include, without limitation, temporary computer memory and permanent computer memory such as RAM, hard drives, CD's, etc.

A second broader expression of the storage medium embodiment is for a storage medium 68 which contains a program readable by a digital computer 20 which instructs the digital computer 20: to receive an indication from a user of a medical target 30 selected for a medical procedure which uses at least a catheter 12 and which is to be performed within the patient 18, wherein the catheter 12 has a catheter distal end 22 inserted into a natural orifice 24 of a body lumen 26 of a patient 18, and wherein a sensor 14 is disposed proximate the catheter distal end 22 and is adapted to provide position data; to display a first image 32 of a first image representation of light-obtained image data 28 from a viewpoint of the catheter distal end 22 wherein the light-obtained image data 28 is obtained proximate the catheter distal end 22; to receive an indication from the user when the catheter distal end 22 is at each of a plurality of predetermined physiological landmarks 34, 36, 38, and 40 spaced apart along and within the body lumen 26; and to indicate to the user position information 44 of the catheter distal end 22 relative to the medical target 30 using at least 3-D image data 16 which is of the patient and which is pre-acquired, the position data, and the indications from the user when the catheter distal end 22 was at each of the plurality of the predetermined physiological landmarks 34-40.

Previously-described implementations, examples, etc. are equally applicable to the second broader expression of the storage medium 68.

Figure 1:
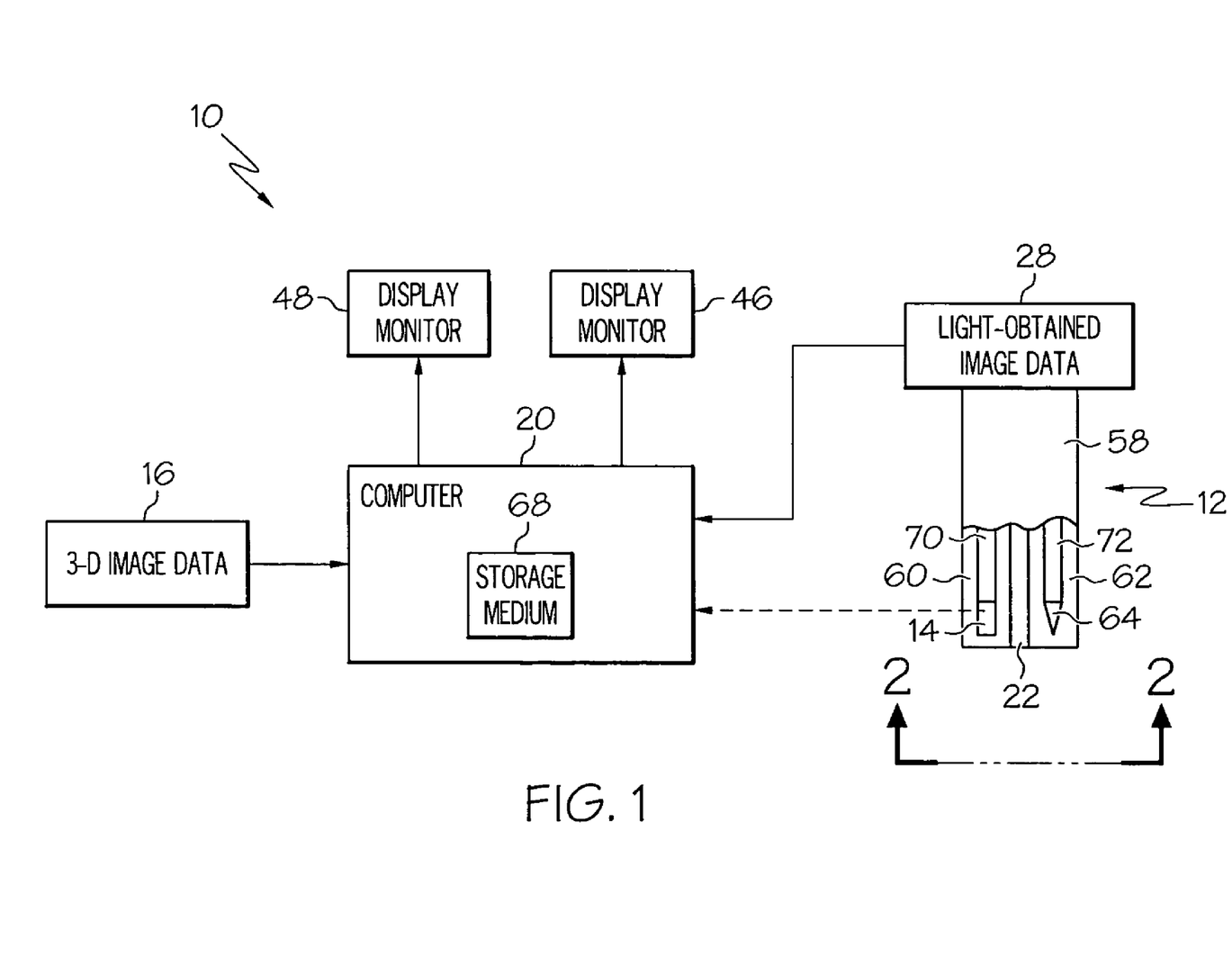
FIG. 1 is a schematic view of an embodiment of a medical system of the invention, wherein the distal-end portion of a catheter (in the from of a gastroscope having two working channels) has been cut away to expose a sensor and a tissue-piercing implement.
Figure 2:
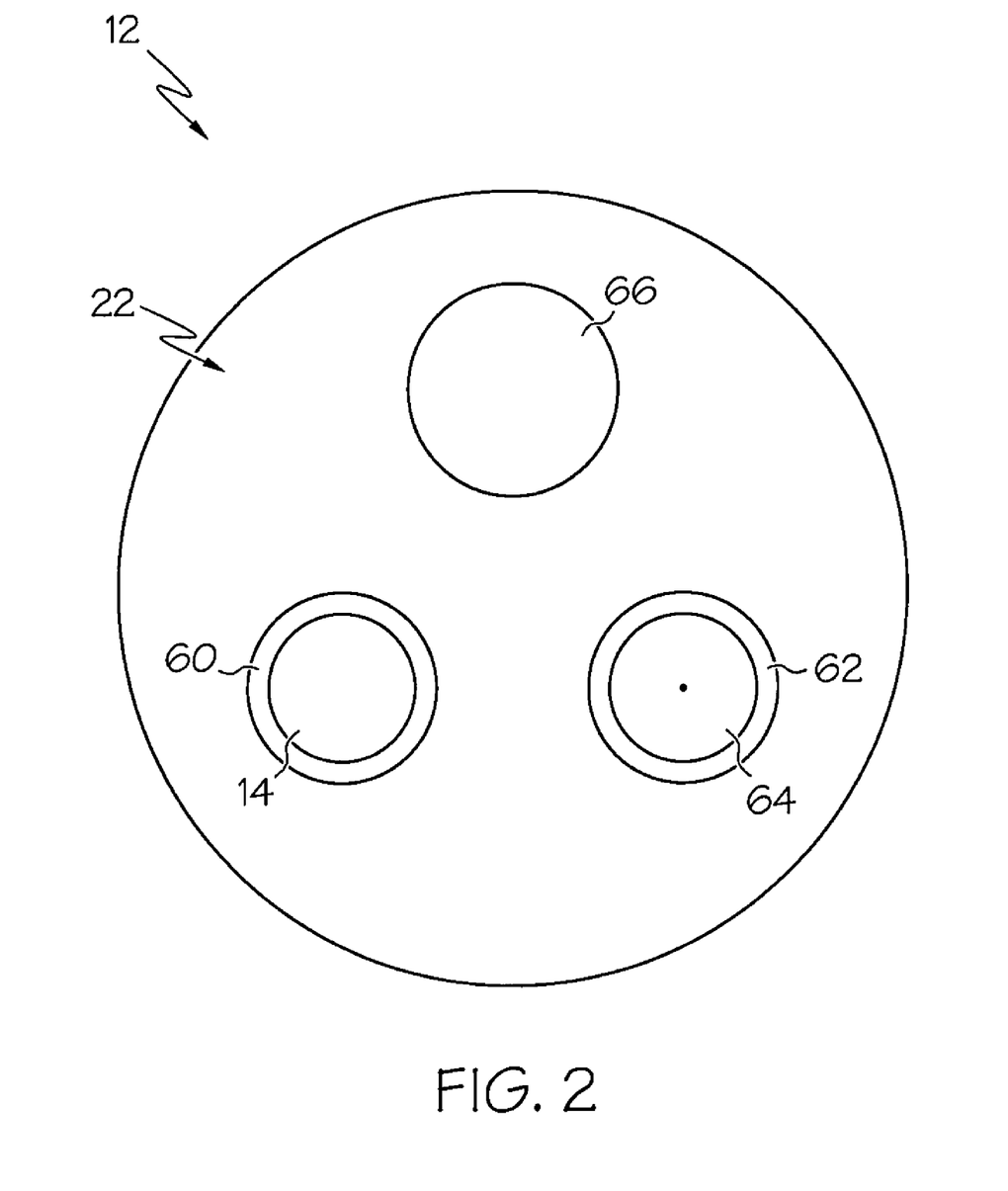
FIG. 2 is an enlarged view of the distal end of the catheter of FIG. 1 taken along lines 2-2 of FIG. 1 showing the sensor disposed in a first working channel of the catheter and showing the tissue-piercing implement disposed in the second working channel of the catheter, wherein scope lighting has been omitted for purposes of clarity.
Figure 3:
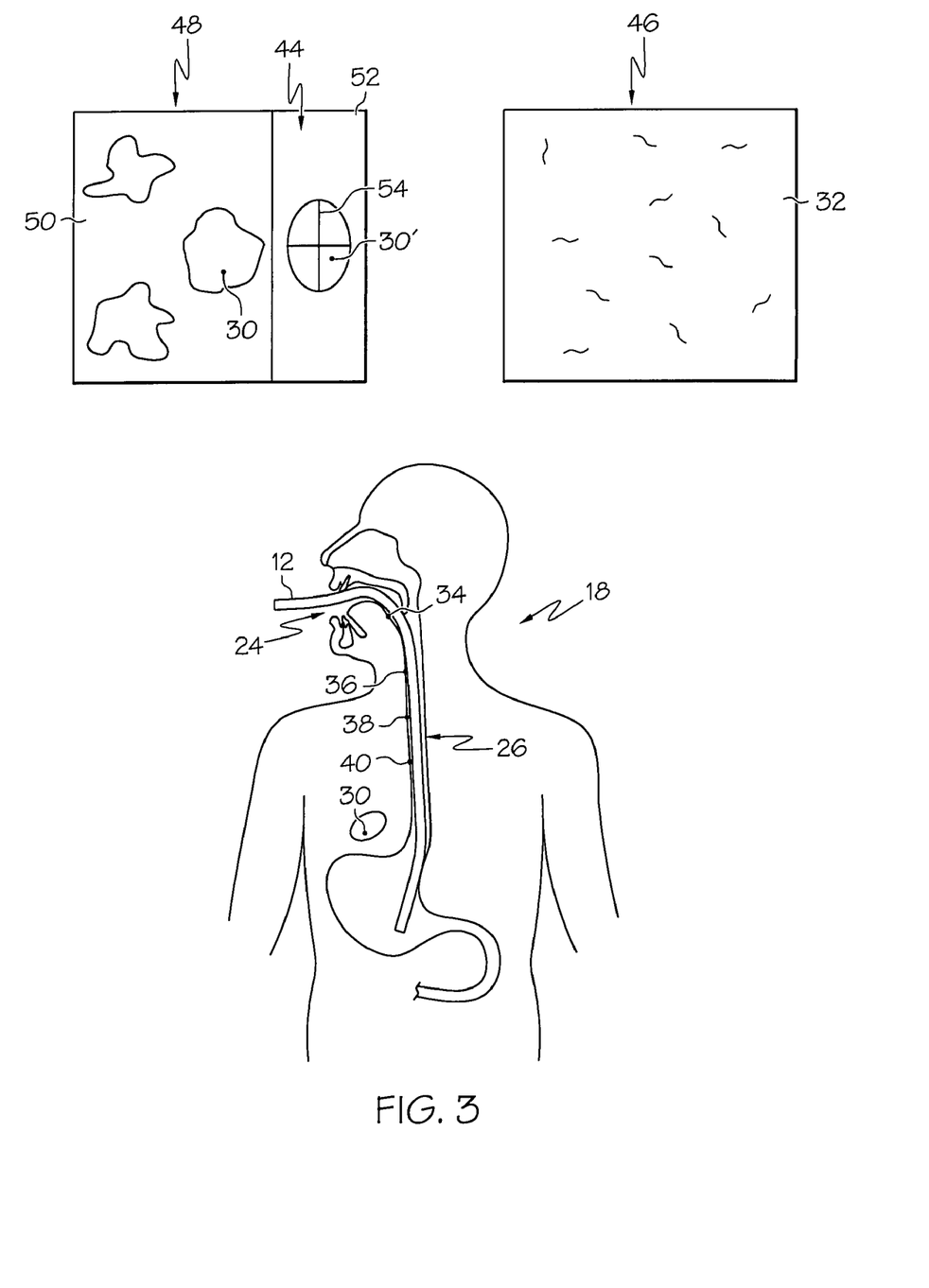
FIG. 3 is a schematic view of a portion of the catheter of FIG. 1 inserted through the esophagus of a patient with the catheter distal end disposed in the stomach and misaligned with a medical target located beyond the stomach wall, wherein FIG. 3 also shows a dynamic image on a first display monitor from the video camera of the catheter, and a dynamic image, corresponding to the video-camera image, on the second display monitor from 3-D image data (such as MRI image data), and wherein the second display monitor also shows an information window which includes a dot representing the location of the medical target and which includes a cross-hairs representing the line-of-sight of the catheter distal end.
Figure 4:
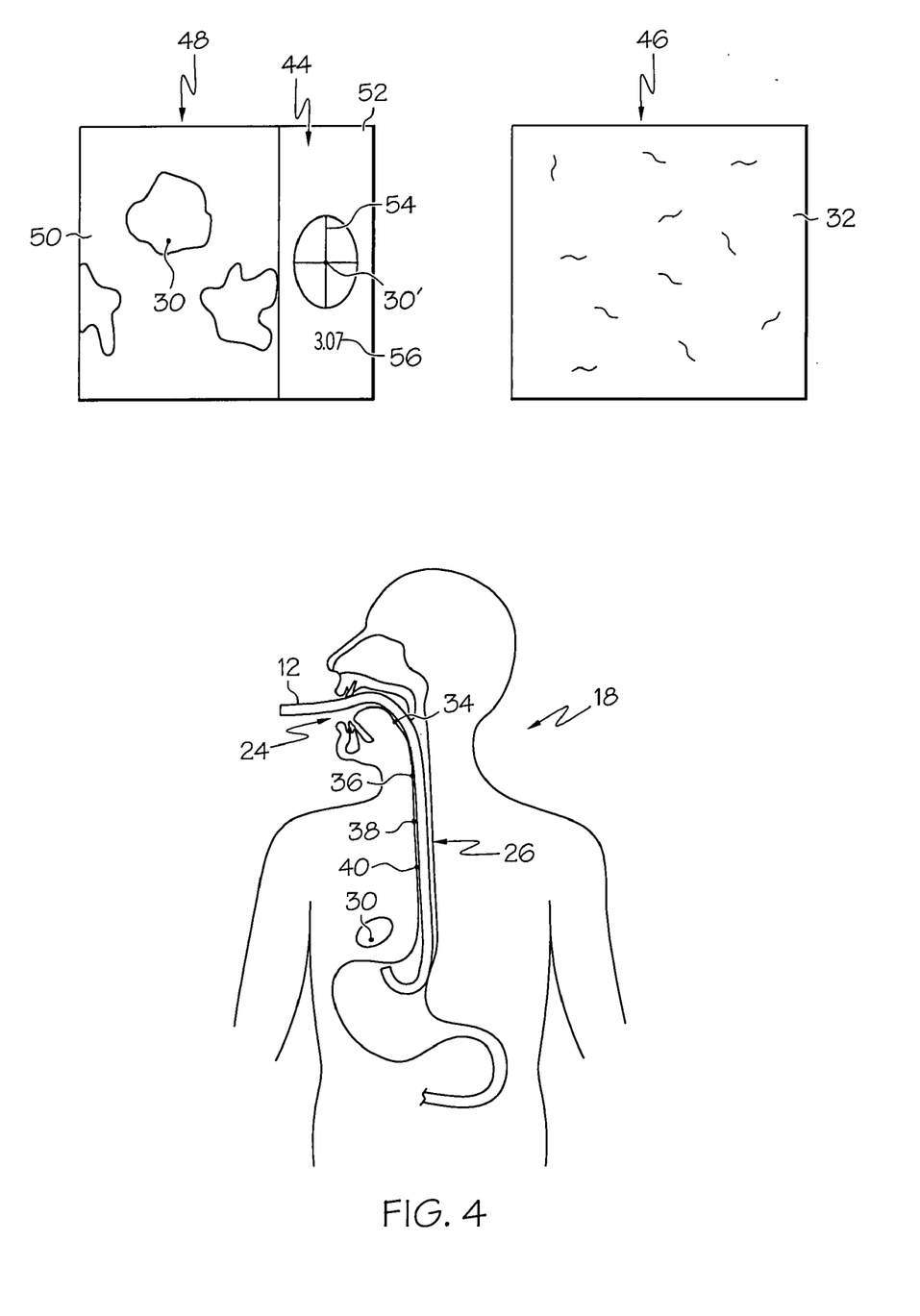
FIG. 4, is a view, as in FIG. 3, but with the catheter distal end aligned with the medical target, with the information window of the second display monitor also showing a number which indicates the distance between the aligned catheter distal end and the medical target.
Figure 5:
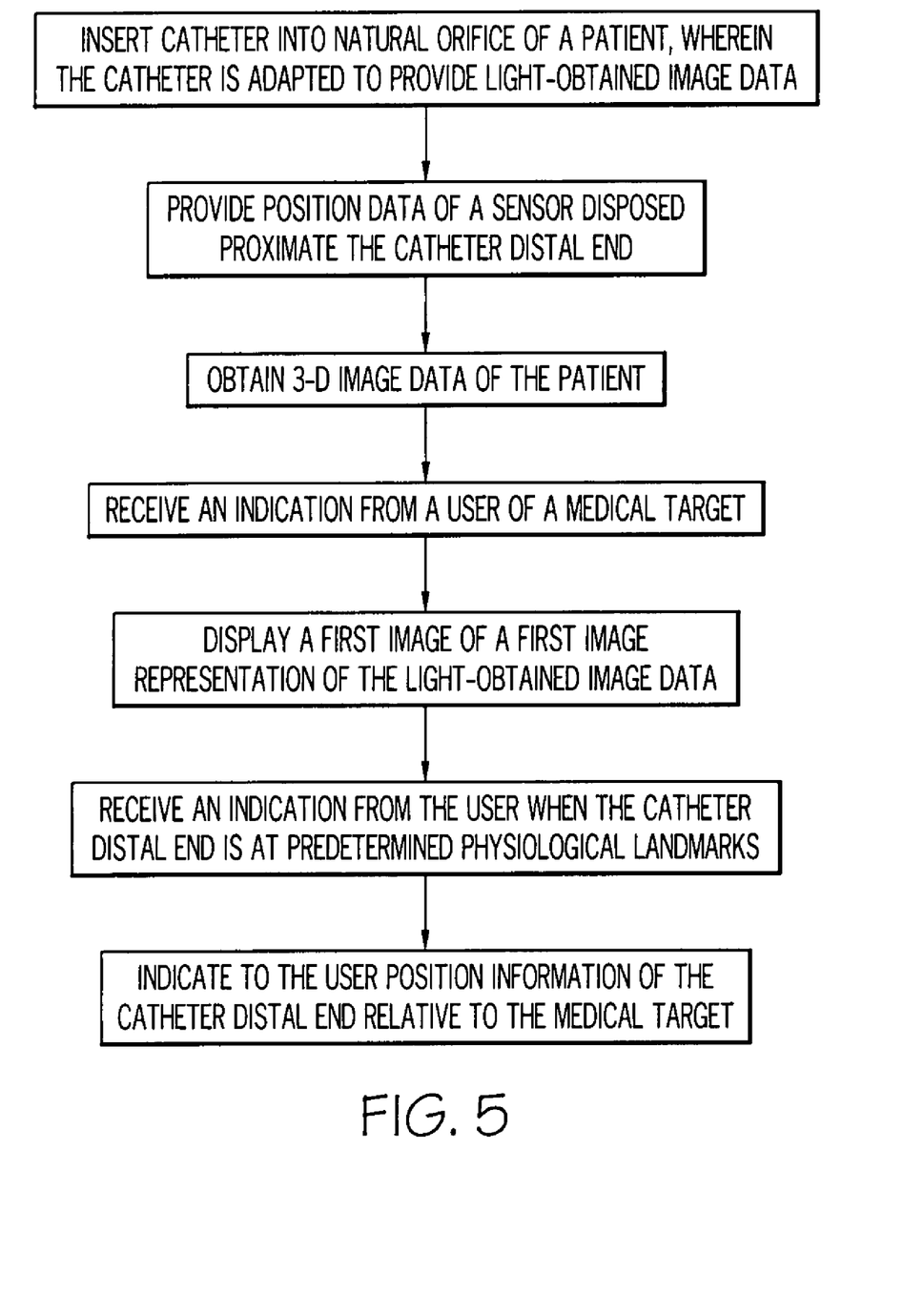
FIG. 5 is a block diagram of a first method of the invention.

A first method of the invention is for a method for assisting a medical procedure, wherein the method is shown in outline form in FIG. 5 and includes: inserting a catheter distal end 22 of a catheter 12 into a natural orifice 24 of a body lumen 26 of a patient 28, wherein the catheter 12 is adapted to provide light-obtained image data 28 obtained from proximate the catheter distal end 22; providing position data of a sensor 14 disposed proximate the catheter distal end 22; obtaining 3-D image data 16 which is of the patient 18 and which is pre-acquired; receiving an indication from a user of a medical target 30 selected for the medical procedure, wherein the medical procedure uses at least the catheter 12 and is to be performed within the patient 18; displaying a first image 32 of a first image representation of the light-obtained image data 28 from a viewpoint of the catheter distal end 22; receiving an indication from the user when the catheter distal end 22 is at each of a plurality of predetermined physiological landmarks 34, 36, 38, and 40 spaced apart along and within the body lumen 26; and indicating to the user position information 44 of the catheter distal end 22 relative to the medical target 30 using at least the 3-D image data 16, the position data, and the indications from the user when the catheter distal end 22 was at each of the plurality of predetermined physiological landmarks 34-40.

Previously-described implementations, examples, etc. are equally applicable to the first method.

Figure 6:
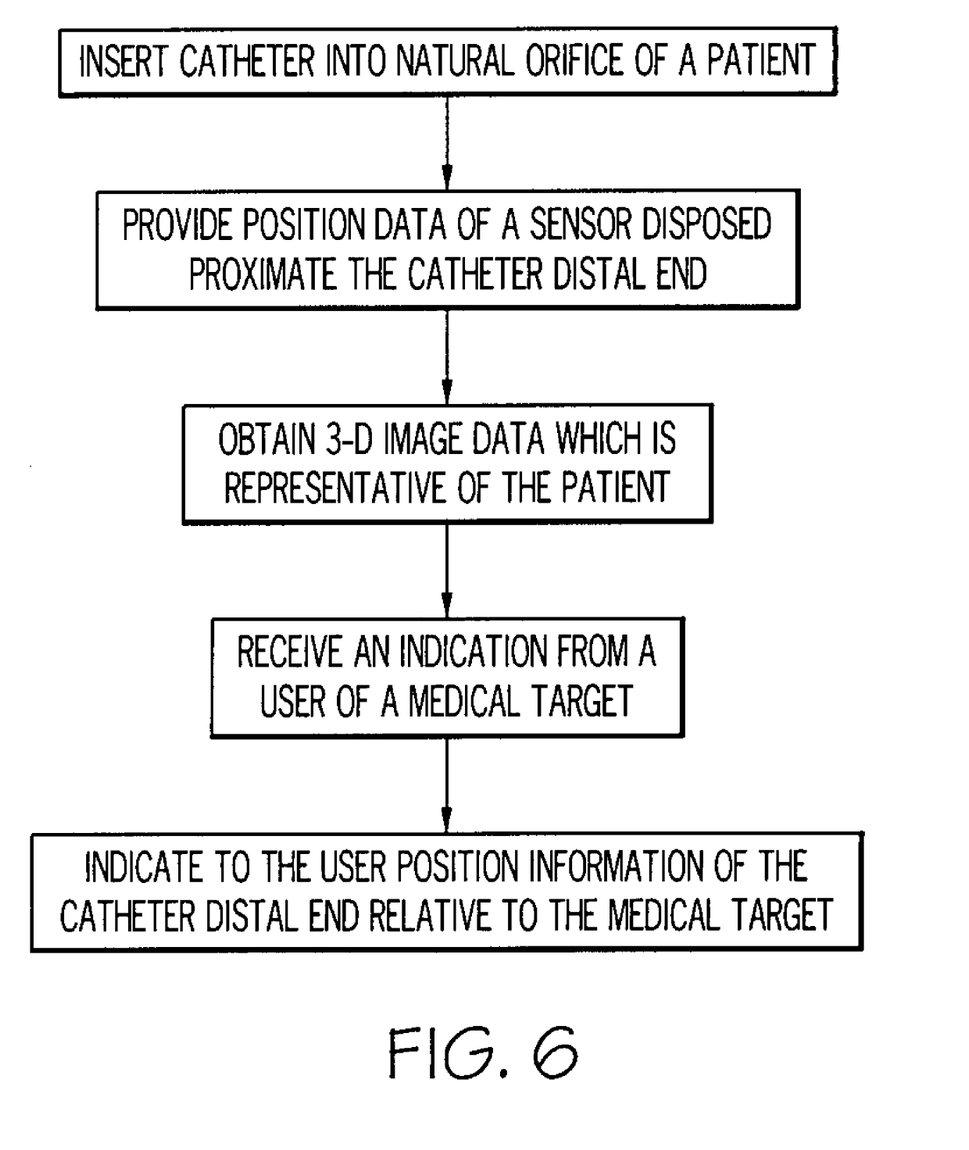
FIG. 6 is a block diagram of a broader second method of the invention.

A broader second method of the invention is for a method for assisting a medical procedure, wherein the method is shown in outline form in FIG. 6 and includes: inserting a catheter distal end 22 of a catheter 12 into a natural orifice 24 of a body lumen 26 of a patient 18; providing position data of a sensor 14 disposed proximate the catheter distal end 22; obtaining 3-D image data 16 which is representative of the patient 18; receiving an indication from a user of a medical target 30 selected for the medical procedure, wherein the medical procedure uses at least the catheter 12 and is to be performed within the patient 18; and indicating to the user position information 44 of the catheter distal end 22 relative to the medical target 30 using at least the 3-D image data 16 and the position data.

Previously-described implementations, examples, etc. are equally applicable to the second method.

In one realization of any one or more or all of the previously described expressions and methods, the position data, the 3-D image data 16 and/or the light-obtained image data 28 are already properly indexed when received by the computer 22. In a different realization, the position data, the 3-D image data 16 and/or the light-obtained image data 28 are not yet indexed, and such indexing is performed by the computer 22.

In one utilization, the 3-D image data 16 is real-time image data, the light-obtained image data 28 is real-time image data, and the position data is real-time position data.

In one deployment, the sensor 14 is disposed distal of any articulation joint of the catheter 12, wherein the catheter 12 from the sensor 14 to the catheter distal end 22 is rigid.

In one arrangement, the time frequency, for the computer 20 to update the first image 32 and the second image 50 is a user input to the computer 20. In a second arrangement, the time frequency is a fixed number. In a third arrangement, the time frequency is determined by the computer 20 based on variables such as, but not limited to, the speed of the catheter 12.

In one technique, an indication of when the catheter distal end 22 is proximate one of the predetermined physiological landmarks 34-40 is sent to the computer 20 by a user such as (but not limited to) by a user moving a foot pedal (not shown) operatively connected to the computer 20. In one variation, the medical target 30 is chosen by the computer 20 based on a user selected medical technique. In a different variation, the user selects the medical target 30 by clicking a mouse when a cursor (not shown) has been placed by the user on an appropriate point on the second image 50 after the user has manipulated the second image to show the medical target to be selected.

In one construction, the sensor 14 is attached to the distal end of a first elongated member 70 which is manipulated by the user to translate the sensor 14 in the first working channel 60 of the insertion tube 58. In this construction, the tissue-piercing implement 64 is attached to the distal end of a second elongated member 72 which is manipulated by the user to translate the tissue-piercing implement 64 in and beyond the second working channel 62 of the insertion tube 58.

Several benefits and advantages are obtained from one or more of the expressions of the embodiment of the system, the expressions of the storage medium, and the methods of the invention. In one example, the catheter is a gastroscope insertion tube whose distal end is disposed in the stomach of a patient, the medical target is a tumor on an organ outside of, but close to, the stomach. In this example, the position information of the insertion-tube distal end relative to the medical target assists the user in aligning the distal end in the stomach a short distance from the tumor. When the indicated alignment and distance are acceptable, the user, in this example, then extends a tissue-piercing implement from a working channel of the gastroscope beyond the insertion-tube distal end to cut through the stomach wall to reach and medically treat the nearby tumor. This avoids having to make an external incision on the patient as is required in open-surgery and laparoscopic procedures.

While the present invention has been illustrated by expressions of a medical system embodiment, expressions of a storage medium containing a program readable by a digital computer, and two methods, and enablements, applications, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A storage medium containing a program readable by a digital computer which instructs the digital computer:

a) to receive an indication from a user of a medical target selected for a medical procedure which uses at least a catheter and which is to be performed within a patient, wherein the catheter has a catheter distal end configured to be inserted into a natural orifice of a body lumen of the patient, and wherein a sensor is disposed proximate the catheter distal end and is adapted to provide position data;

b) to receive an indication from the user when the catheter distal end is at each of a plurality of predetermined physiological landmarks spaced apart along and within the body lumen, and to calculate a position of the sensor indexed to the patient by calculating a position of the sensor indexed to a reference coordinate system and by indexing the reference coordinate system to the patient using at least the position data and the indications from the user when the catheter distal end was at each of the plurality of predetermined physiological landmarks;

c) to create a first image representation of the patient indexed to the patient and from a viewpoint of the catheter distal end, through light-obtained image data obtained proximate the catheter distal end, using at least the light-obtained image data and the calculated position of the sensor indexed to the patient, and to display on one of at least-one display monitor a first image of the first image representation;

d) to indicate to the user position information of the catheter distal end relative to the medical target using at least 3-D image data which is of the patient and is pre-acquired, the position data, and the indications from the user when the catheter distal end was at each of the plurality of the predetermined physiological landmarks; and e) to create a second image representation of the patient indexed to the patient from a viewpoint of the catheter distal end, using at least the 3-D image data, the indications from the user when the catheter distal end was at each of the plurality of predetermined physiological landmarks, and the calculated position of the sensor indexed to the patient, with the second image representation visually corresponding to the first image representation, and to display on one of the at least-one display monitor a second image of the second image representation.

2. The storage medium of claim 1, wherein the program instructs the digital computer:

to identify the physiological landmarks within the 3-D image data.

3. The storage medium of claim 2, wherein the at-least-one display monitor includes first and second display monitors, wherein the first image is displayed on the first display monitor, and wherein the second image is displayed on the second display monitor.

4. The storage medium of claim 3, wherein the program instructs the digital computer to morph the second image representation using the first image representation as a reference image representation.

5. The storage medium of claim 3, wherein the position information includes alignment information of the catheter distal end relative to the medical target and includes distance information of the catheter distal end relative to the medical target when the catheter distal end is aligned with the medical target.

6. The storage medium of claim 3, wherein the program instructs the digital computer to display in the second image only user-selected ones of body systems and organs thereof from the 3-D image data.

7. The storage medium of claim 3, wherein the medical target is located outside the body lumen.

8. The storage medium of claim 3, wherein the 3-D image data are chosen from the group consisting of ultrasound image data, X-ray image data, computerized tomography (CT) image data, positive electron emission (PET) image data, magnetic resonance (MRI) image data, and fluoroscope image data.

* * * * *